United States Patent [19]

Blank et al.

[11] Patent Number: 4,567,004

[45] Date of Patent: Jan. 28, 1986

[54] PROCESS FOR THE PREPARATION OF MONOMETHYL-SUBSTITUTED METHYLENE COMPOUNDS

[75] Inventors: Heinz U. Blank, Odenthal; Erich Wolters, Niederzier, both of Fed. Rep. of Germany

[73] Assignee: Bayer Aktiengesellschaft, Leverkusen, Fed. Rep. of Germany

[21] Appl. No.: 632,134

[22] Filed: Jul. 18, 1984

[30] Foreign Application Priority Data

Jul. 23, 1983 [DE] Fed. Rep. of Germany ....... 3326635

[51] Int. Cl.$^4$ ................. C07C 121/66; C07C 121/20; C07C 121/34; C07C 121/407
[52] U.S. Cl. ................. 260/465 R; 568/396; 568/932; 260/239 BC; 568/944; 562/429; 260/456 R; 562/434; 562/459; 260/456 A; 562/480; 562/553; 260/456 P; 562/577; 562/590; 260/465 D; 562/607; 564/82; 260/465 E; 564/85; 564/87; 260/465 H; 564/88; 564/95; 260/465.1; 564/162; 564/166; 260/465.5 R; 564/169; 564/192; 260/465.4; 564/193; 564/199; 260/465.8 R; 260/505 R; 260/513 R; 544/299; 549/267; 560/11; 560/14; 560/20; 560/51; 560/81; 560/149; 560/150; 560/156; 560/178; 560/190; 568/30; 568/31; 568/306; 568/307; 568/318; 568/376; 568/379
[58] Field of Search ................. 260/465.4, 465.8 R, 260/239 BC, 456 R, 465 R; 560/190, 81, 156, 178; 544/299; 549/267; 562/590, 607; 568/376, 379, 396

[56] References Cited

U.S. PATENT DOCUMENTS 3,956,357 5/1976 Kaye et al. ................. 260/465.4

Primary Examiner—Dolph H. Torrence
Attorney, Agent, or Firm—Sprung, Horn, Kramer & Woods

[57] ABSTRACT

Monomethyl-substituted methylene compounds are obtained by reacting methylene compounds of the formula

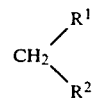

in which
  $R^1$ and $R^2$ independently of one another represent —CN, —CO—$R^3$, —SO$_2$—$R^3$ or —NO$_2$ and
  $R^1$ can additionally denote -aryl($R^1$)$_n$,
wherein
  $R^3$ denotes —OH, alkyl, aralkyl, aryl, alkoxy, aralkoxy or aryloxy, or amino which is substituted by alkyl and/or aralkyl and/or aryl, and furthermore two radicals $R^3$ together can be an alkylene group, the radical of an aliphatic diol or of an aliphatic diamine or the group —NH—CO—NH— and n represents 1, 2 or 3, with formaldehyde and with hydrogen in the presence of a condensation catalyst and a hydrogenation catalyst at elevated temperature, the methylene compound being introduced into the liquid phase of the mixture of reactants in the course of the reaction.

23 Claims, No Drawings

PROCESS FOR THE PREPARATION OF MONOMETHYL-SUBSTITUTED METHYLENE COMPOUNDS

It is known that C-H acid compounds, such as cyanoacetates, malonates or acetoacetates, can be reacted with methyl halides, such as methyl bromide, or with methyl esters, such as dimethyl sulphate, to give the monomethylated compounds. A great disadvantage of this procedure is that mixtures of the monomethylated compounds with the starting compound and the dimethylated product are always obtained and, because the boiling points differ only slightly, these can be separated only by great expenditure on distillation. This process is thus not particularly suitable for the preparation of pure monomethylated compounds.

The method of condensing these compounds with aldehydes or ketones to give the alkylidene derivatives and then converting these into the desired alkyl derivatives by hydrogenation is also known, by the name of "reductive alkylation", for alkylation of C-H acid compounds (Org. Reactions 9, pages 145, 146). This reaction is advantageously carried out in one stage, and the hydrogenation of the alkylidene derivatives, which tend to polymerize, can be carried out in the presence of hydrogen and a hydrogenation catalyst directly after the condensation. The monoalkyl derivatives are obtained in high yields (frequently above 90% of the theoretical yield), especially if lower aliphatic aldehydes are used (J. Am. Chem. Soc. 66, 886-888 (1944); German Offenlegungsschrift 2,060,443). In contrast to the use of other lower aliphatic aldehydes, however, methylation using formaldehyde leads to significantly lower yields. Thus, yields of only 40-45% for the methylation of acetoacetates by this process are described in German Offenlegungsschrift No. 2,060,443. Yields of between 14 and 61% for the methylation of cyanoacetates by this process are mentioned in German Offenlegungsschrift No. 2,515,039. In all the cases described, the reaction is carried out by taking the reactants together, or by adding the formaldehyde to a mixture of the other reactants in the course of the reaction.

A process has now been found for the preparation of monomethyl-substituted methylene compounds of the formula

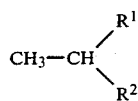   (I)

by methylation of methylene compounds of the formula

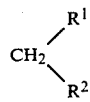   (II)

in which
R$^1$ and R$^2$ independently of one another represent —CN, —CO—R$^3$, —SO$_2$—R$^3$ or —NO$_2$ and
R$^1$ can additionally denote -aryl(R$^1$)$_n$,
wherein
R$^3$ denotes —OH, alkyl, aralkyl, aryl, alkoxy, aralkoxy or aryloxy, or amino which is optionally substituted by alkyl and/or aralkyl and/or aryl, and furthermore
two radicals R$^3$ together can be an alkylene group, the radical of an aliphatic diol or of an aliphatic diamine or the group —NH—CO—NH— and n represents 1, 2 or 3,
by reaction with formaldehyde and hydrogen in the presence of a condensation catalyst and a hydrogenation catalyst at elevated temperature, which is characterized in that the methylene compound is introduced into the liquid phase of the mixture of reactants in the course of the reaction.

As alkyl there may be mentioned a straight-chain or branched aliphatic hydrocarbon radical with 1-10, preferably 1-4 and particularly preferably 1-2, carbon atoms, such as alkyl e.g., methyl, ethyl, propyl, isopropyl, butyl, isobutyl, tert.-butyl, hexyl, octyl or decyl.

Examples of aralkyl which may be mentioned are benzyl, phenethyl and phenylpropyl, preferably benzyl.

Examples of aryl which may be mentioned are phenyl and naphthyl, preferably phenyl, it being possible for the aromatic nucleus, as also in the aralkyl radicals mentioned, also to be substituted by C$_1$-C$_4$-alkyl, C$_1$-C$_4$-alkoxy, C$_1$-C$_4$-alkylamino or halogen, such as fluorine, chlorine, bromine or iodine, preferably fluorine or chlorine.

Examples of alkoxy, aralkoxy and aryloxy which may be mentioned are the abovementioned alkyl, aralkyl or aryl radicals supplemented by an oxygen atom, the preferred ranges mentioned for the number of C atoms applying.

The index n can assume the numerical value of 1, 2 or 3, the numerical value of 1 being preferred. Of the substituents R$^1$, characterized by the index n, for the aryl radical, at least one is preferably in the o- or p-position.

Two radicals R$^3$ can furthermore together be an alkylene group, for example with 2-5, preferably 3-4, C atoms, the radical of an aliphatic diol or aliphatic diamine, for example with in each case 2-4, preferably 2 or 3, C atoms, or the group —NH—CO—NH—. Cyclic methylene compounds, which can be reacted according to the invention, are formed by such a configuration. The H atoms on the C or N atoms of such ring members formed by two radicals R$^3$ can, of course, be replaced by inert atoms or groups, such as, for example, fluorine, chlorine, bromine, C$_1$-C$_4$-alkyl, C$_1$-C$_4$-alkoxy or C$_1$-C$_4$-alkylamino.

Preferred methylene compounds which can be used according to the invention are those of the formula

   (III)

in which
R$^1$ has the abovementioned meaning and
R$^4$ represents —CN or —CO—R$^3$,
wherein
R$^3$ likewise has the abovementioned meaning.

Methylene compounds which are particularly preferably used are those of the formula

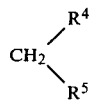
(IV)

in which
R$^4$ and R$^5$ independently of one another represent —CN or —CO—R$^3$,
wherein
R$^3$ has the abovementioned meaning.

Methylene compounds which are very particularly preferably employed are those of the formula

(V)

in which
R$^6$ and R$^7$ independently of one another denote —CN, —CO—C$_1$-C$_4$-alkyl or —CO—O—C$_1$-C$_4$-alkyl.

Examples of compounds which can be used according to the invention are: malodinitrile, cyanoacetates with various alcohol radicals, acetoacetates with various alcohol radicals, nitroacetates with various alcohol radicals, malonates with various alcohol radicals, malonic acid, cyanoacetic acid, acetic acid, cyclopentane-1,3-dione, cyclohexane-1,3-dione, cyclic ethylene glycol malonates, cyclic malonic acid ethylene-diamide, barbituric acid, acetylacetone, cyanomethanesulphonates with various alcohol radicals, 4-nitrobenzyl cyanide, 2,4-dinitrobenzyl cyanide and 4-carbethoxyphenylacetates with various alcohol radicals.

The process according to the invention can be carried out under a partial pressure of hydrogen of 1-100 bar. The preferred pressure range is from 3 to 50 bar, particularly preferably from 5 to 15 bar.

Suitable hydrogenation catalysts are all the customary noble metal catalysts, such as palladium, platinum, rhodium and ruthenium, preferably on supports, such as silicic acid, aluminum oxide or charcoal. It is also possible to use Raney nickel or Raney cobalt and related Raney catalysts. A catalyst of palladium-on-charcoal is preferably used, and particularly preferably with a palladium content of 3-5% by weight of the total supported catalyst. The amount of catalyst can be 1-20% by weight, based on the methylene compound employed. 3-10% by weight, preferably 4-6% by weight, of catalyst, based on the methylene compound employed, is frequently sufficient.

The reaction temperature is 30°-130° C., preferably 60°-100° C. and particularly preferably 80°-90° C.

Condensation catalysts which can be used are those which catalyze reactions of the aldol condensation type. Examples of such catalysts are amines, such as piperidine, morpholine, pyrrolidine, triethylamine or other tertiary amines, or basic salts, for example of organic acids, such as sodium acetate or potassium oxalate, or carboxylic acids, such as formic acid or acetic acid, or hydrogen chloride, sulphuric acid or Lewis acids, such as zinc chloride, aluminium chloride or iron chloride.

Tertiary amines, the basic salts mentioned or acetic acid are preferably used as the condensation catalysts. The amount of condensation catalyst employed is is general 1-10 mol %, based on the methylene compound employed, preferably 3-6 mol %. The optimum condensation catalyst and the optimum amount of catalyst for a specific case may easily be determined by preliminary experiments.

The formaldehyde can be used in the form of paraformaldehyde, formaldehyde gas or formaldehyde solution, for example in alcohols, such as methanol. It is preferably used in the form of paraformaldehyde. In the solvents mentioned, paraformaldehyde is partly in suspension and partly dissolved in the depolymerized form. The depolymerization can be accelerated, for example, by addition of small amounts of cyanide ions. The formaldehyde is employed in equimolar amounts or in an excess of up to 10 mol %, based on the methylene compound. A molar excess of 5-10% of formaldehyde is preferably employed. Larger excesses of formaldehyde are possible, but in general provide no further increase in the yield, whilst amounts smaller than equimolar amounts of formaldehyde lead to incomplete conversion of the methylene compound.

According to the invention, the methylene compound is added to the mixture of the initially introduced reactants formaldehyde, condensation catalyst, hydrogenation catalyst and hydrogen, which have first been brought to the desired reaction temperature. This addition is in general effected approximately at the rate at which the reaction progresses, or somewhat more slowly than the reaction progresses. The progress of the reaction can be monitored in a simple manner from the consumption of the hydrogen. This is effected, for example, by keeping the pressure constant during the reaction and determining the amount of hydrogen required to maintain constant pressure via a flow meter, such as rotameter. The methylene compound can be added here in suitable small portions or almost continuously, for example via a metering pump. To monitor the progress of the reaction, it is assumed that, for hydrogenation of the condensation compound formed from formaldehyde and the methylene compound in the reaction mixture, one mol of hydrogen is used for the hydrogenation per mol of methylene compound.

The process according to the invention is carried out in the liquid phase. Examples of solvents or diluents which may be mentioned are: Lower alcohols, such as methanol, ethanol, propanol and butanol, esters of organic acids, such as ethyl acetate, nitriles, such as acetonitrile, organic acids, such as acetic acid, ketones, such as acetone and methyl ethyl ketone, and other solvents, such as, for example, water. Lower alcohols, such as methanol or ethanol, ethyl acetate or methyl ethyl ketone are preferably used, and methanol is particularly preferred. Whilst water produces more unfavourable results than the organic solvents or diluents mentioned when it is used as the solvent for readily hydrolyzable compounds, it is not necessary to remove the water formed in the condensation reaction from the reaction mixture. On the other hand, water can advantageously be used as the reaction medium for compounds which are difficult to hydrolyze, such as, for example, barbituric acid. The amount of solvent or diluent employed can be varied within wide limits. An amount of 50-2,000 ml per mol of methylene compound, preferably an amount of 150-1,000 ml and particularly preferably an amount of 250-500 ml, may be mentioned by way of example.

All or some of the solvent or diluent may be taken with the other reactants to be initially introduced into the reaction vessel, in the latter case the remainder serving to dissolve or dilute the methylene compound to be metered in.

The process according to the invention is carried out, for example, by initially introducing paraformaldehyde, the condensation catalyst and the hydrogenation catalyst in the solvent or diluent into an autoclave. The reaction mixture is then brought to the desired reaction temperature, with stirring, and hydrogen is forced in to the desired partial pressure. The methylene compound is then pumped into the autoclave in concentrated or dilute form. The optimum rate at which this compound is pumped in is as far as possible suited to the rate of reaction, which can be observed from the progress of the hydrogenation in the manner described and can be matched to the desired temperature, the desired dilution, the desired hydrogen pressure and the nature and amount of the catalysts in preliminary experiments. After all of the methylene compound has been pumped in, stirring is in general continued for some time, during which a slight subsequent uptake of hydrogen is sometimes also observed. After the autoclave has been cooled and let down, the hydrogenation catalyst is filtered off and the filtrate is separated into its components by distillation, crystallization or another suitable method of working up. In the case where the methylene compound is very sparingly soluble in the chosen solvent, it can already be taken at the start together with the other reactants. According to the invention, the methylene compound in this case also only passes into the liquid phase in the course of the reaction, and is reacted there.

EXAMPLE 1

48.5 g (1.58 mol) of powdered paraformaldehyde (98% pure), 3.3 g (0.04 mol) of sodium acetate and 8.0 g of a 5% strength Pd/C catalyst in 300 ml of methanol are initially introduced into a 1.3-liter V4A autoclave. The autoclave is flushed with nitrogen and heated to 80° C., with stirring. A hydrogen pressure of 10 bar is established and a solution of 143.0 g (1.44 mol) of methyl cyanoacetate in 400 ml of methanol is pumped in over a period of 2 hours. The pressure of 10 bar is maintained by subsequently adding hydrogen via a reducing valve. Stirring is then continued until the uptake of hydrogen has ended (about 3 hours). After the autoclave has been cooled to room temperature, it is let down and the contents are filtered off from the catalyst, which can be washed with methanol and used again. The clear pale yellow filtrate is dried over sodium sulphate and distilled over a 30 cm Vigreux column. After the methanol has been distilled off under normal pressure, the entire residue is distilled over under 16 mbar. 153.7 g of distillate, which, according to analysis by gas chromatography, contains 99.5% of methyl 2-cyanopropionate, are obtained at an overhead temperature between 80° and 90° C. This corresponds to a yield of 94.0% of the theoretical yield, based on the methyl cyanoacetate employed. 6 g of a highly viscous residue remain in the distillation flask.

EXAMPLE 2

The procedure is as in Example 1. However, instead of sodium acetate, 3.3 g (0.06 mol) of acetic acid are used, and instead of the methyl cyanoacetate, 167.2 g (1.44 mol) of methyl acetoacetate in methanolic solution are pumped in. After the methanol and acetic acid have been distilled off during working up of the batch, 189.0 g of 95% pure methyl 2-methylacetoacetate are obtained. This corresponds to a yield of 95.9% of the theoretical yield, based on the methyl acetoacetate employed.

The distillate contains 2.1% of methyl 2-methoxymethylacetoacetate as a by-product. A residue of 3.0 g remains in the distillation flask.

EXAMPLE 3

The procedure followed is as in Example 2, but 230.4 g (1.44 mol) of diethyl malonate are pumped in instead of the methyl acetoacetate. After analogous working up, 230.0 g of 90% pure diethyl methylmalonate are obtained on distillation. This corresponds to a yield of 82.6% of the theoretical yield, based on the diethyl malonate employed. The distillate also contains 9.3% of diethyl methoxymethylmalonate as a by-product. A residue of 3.1 g remains in the distillation flask.

EXAMPLE 4

The procedure followed is as in Example 1, but 144.0 g (1.44 mol) of acetylacetone are pumped in instead of the methyl cyanoacetate. 147.4 g of 98% pure 3-methylpentane-2,4-dione are obtained on distillation. This corresponds to a yield of 88.0% of the theoretical yield, based on acetylacetone employed. The distillate contains 1.3% of 3-methoxymethylpentane-2,4-dione. A residue of 10.3 g remains in the distillation flask.

EXAMPLE 5

11.3 g (0.37 mol) of powdered paraformaldehyde (98% pure), 0.8 g (0.01 mol) of sodium acetate and 3.7 g of a 5% strength Pd/C catalyst in 200 ml of methyl ethyl ketone are initially introduced into a 1.3-liter V4A autoclave. The autoclave is flushed with nitrogen and heated to 80° C., with stirring. A hydrogen pressure of 10 bar is established and a solution of 54 g (0.33 mol) of 4-nitrobenzyl cyanide in 370 ml of methyl ethyl ketone is pumped in over a period of 2 hours.

The temperature and hydrogen pressure are maintained until the uptake of hydrogen has ended (about 1.5 hours). On distillation, 29 g of a product which consists of 2-(4-nitrophenyl)-propionitrile to the extent of 97% and starting substance to the extent of 3% are obtained at 150°–160° C./1.3 mbar. This product can be recrystallised from methanol and has a melting point of 74°–75° C. Yield: 48.4%.

EXAMPLE 6

The procedure followed is as in Example 1, and 95.0 g (1.44 mol) of malodinitrile in methanolic solution are pumped in instead of the methyl acetoacetate. After analogous working up, 95.1 g of 93% pure methyl malodinitrile are obtained on distillation. Methoxymethylmalodinitrile is formed as a by-product. The distillation residue is 6.5 g. The yield is 77% of the theoretical yield.

EXAMPLE 7

184 g (1.44 mol) of barbituric acid, 48.5 g (1.58 mol) of powdered paraformaldehyde (98% pure), 3.3 g (0.04 mol) of sodium acetate and 16 g of a 5% strength Pd/C catalyst are suspended in 700 ml of water in a 1.3-liter V4A autoclave. The autoclave is flushed with nitrogen and heated to 80° C., with stirring. A hydrogen pressure of 10 bar is established and the autoclave is stirred until the pressure remains constant.

1 liter of water is added to the contents removed from the autoclave. The mixture is heated to the reflux temperature and the undissolved material is filtered off hot. 130.7 g of 5-methylbarbituric acid (melting point: 205°–217° C.) crystallise out of the filtrate. A further 75.9 g (melting point: 195°–202° C.) are obtained on concentration of the mother liquor.

COMPARISON EXAMPLES

If the experiments described in Examples 1–5 are carried out not by pumping in the methylene compound but by taking it with the other reactants and proceeding otherwise as described in the examples, the following results are obtained:

COMPARISON TO EXAMPLE 1

After all the methanol has been distilled off, 175.7 g of a viscous residue which cannot be distilled under 16 mbar up to a bottom temperature of 200° C. are obtained. Only traces of methyl cyanoacetate and methyl 2-cyanopropionate can be detected in the methanol distilled off.

COMPARISON TO EXAMPLE 2

After all the methanol has been distilled off, 90.5 g of distillate containing 84.3% of methyl 2-methylacetoacetate are obtained. This corresponds to a yield of 45.7% of the theoretical yield, based on the methyl acetoacetate employed. In addition to a little methyl acetoacetate, the distillate contains 9.1% of methyl 2-methoxymethylacetoacetate. A non-distillable residue of 77.5 g remains.

COMPARISON TO EXAMPLE 3

After the alcohol has been distilled off, 229.1 g of distillate containing 10.5% by weight of diethyl methylmalonate, 82.7% by weight of diethyl malonate and 3.3% by weight of diethyl methoxymalonate are obtained. This corresponds to a yield of 9.6% of the theoretical yield, based on the diethyl malonate employed. A residue of 1.5 g remains in the distillation flask.

COMPARISON TO EXAMPLE 4

After all the methanol has been distilled off, 69.5 g of distillate containing 88.3% by weight of 3-methylpentane-2,4-dione and various higher-boiling components are obtained. This corresponds to a yield of 37.4% of the theoretical yield, based on the acetylacetone employed. A distillation residue of 81.4 g remains.

COMPARISON TO EXAMPLE 5

After the solvent has been distilled off, 57.4 g of a residue which, according to NMR spectroscopy and analysis by thin layer chromatography, contains only traces of 2-(4-nitrophenyl)-propionitrile remain.

COMPARISON TO EXAMPLE 6

After all the methanol has been distilled off, 102 g of a dark brown, viscous residue which smells strongly of amine and cannot be distilled are obtained.

What is claimed is:

1. A process for the preparation of a monomethyl-substituted methylene compound of the formula

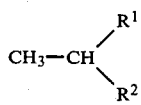

which comprises contacting a methylene compound of the formula

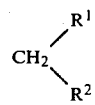

wherein
  $R^1$ and $R^2$ independently of one another represent —CN, —CO—$R^3$, —SO$_2$—$R^3$ and —NO$_2$ and
  $R^1$ can additionally denote —aryl $(R^1)_{n'}$
wherein
  $R^3$ denotes —OH, alkyl, aralkyl, aryl, alkoxy, aralkoxy or aryloxy, or amino which is unsubstituted or substituted by alkyl and/or aralkyl and/or aryl, and furthermore two radicals $R^3$ together can be an alkylene group, the radical of an aliphatic diol or of an aliphatic diamine or the group —NH—CO—NH— and n represents 1, 2 or 3,
with formaldehyde and hydrogen in the presence of a condensation catalyst and a hydrogenation catalyst at elevated temperature, wherein the methylene compound is introduced into a liquid phase of the mixture of reactants over the course of the reaction.

2. A process according to claim 1, wherein the reaction is carried out in the presence of methanol, ethanol, ethyl acetate or methyl ethyl ketone as solvent.

3. A process according to claim 1, wherein the process is carried out in the presence of methanol.

4. A process according to claim 1, wherein formaldehyde is employed in the form of paraformaldehyde.

5. A process according to claim 1, wherein the methylene compound is one of the formula

in which
  $R^1$ has the meaning given in claim 1 and
  $R^4$ represents —CN or —CO—$R^3$,
wherein
  $R^3$ has the meaning given in claim 1.

6. A process according to claim 1, wherein the methylene compound is one of the formula

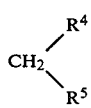

in which
  $R^4$ and $R^5$ independently of one another represent —CN or —CO—$R^3$
wherein
  $R^3$ has the meaning given in claim 1.

7. A process according to claim 1, wherein the methylene compound is one of the formula

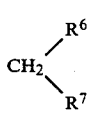

in which

R⁶ and R⁷ independently of one another denote —CN, —CO—$C_1$—$C_4$-alkyl or CO—O—$C_1$-$C_4$-alkyl.

8. A process according to claim 1, wherein the process is carried out at a temperature of 30° to 130° C.

9. A process according to claim 1, wherein the process is carried out under a partial pressure of hydrogen or 1 to 100 bar.

10. A process according to claim 8, wherein the process is carried out under a hydrogen partial pressure of 1 to 100 bar.

11. A process according to claim 1, wherein the hydrogenation catalyst is a noble metal catalyst.

12. A process according to claim 11, wherein the catalyst comprises platinum, palladium, rhodium, or ruthenium on a support.

13. A process according to claim 1, wherein the condensation catalyst is a catalyst which catalyzes reactions of the aldol condensation type.

14. A process according to claim 13, wherein the condensation catalyst is an amine or basic salt or carboxylic acid or hydrogen chloride, sulfuric acid or a Lewis acid.

15. A process according to claim 1, wherein the methylene compound is methyl cyano acetate.

16. A process according to claim 1, wherein said methylene compound is diethyl malonate.

17. A process according to claim 1, wherein said methylene compound is acetyl acetone.

18. A process according to claim 1, wherein said methylene compound is 4-nitrobenzyl cyanide.

19. A process according to claim 1, wherein said methylene compound is malodinitrile.

20. A process according to claim 1, wherein said methylene compound is, malodintrile, a cyano acetate with an alcohol radical, an acetoacetate with an alcohol radical, a nitroacetate with an alcohol radical, a malonate with an alcohol radical, malonic acid, cyanoacetic acid, acetic cyclic ethylene glycol malonate, cyclic malonic acid ethylene-diamide, barbituric acid, acetylacetone, a cyanomethanesulphonate with an alcohol radical, 4-nitrobenzyl cyanide, 2,4-dinitrobenzyl cyanide and a 4-carbethoxyphenylacetate with an alcohol radical.

21. A process according to claim 1, wherein said methylene compound is added to the liquid phase after a desired reaction temperature is attained.

22. A process according to claim 1, wherein said methylene compound is added at a rate at which the reaction progresses, or somewhat more slowly than the reaction progresses.

23. A process according to claim 1, wherein said methylene compound is metered into the liquid phase at a rate corresponding to the rate of hydrogen consumption.

* * * * *